United States Patent [19]

Netherly

[11] Patent Number: 5,797,902
[45] Date of Patent: Aug. 25, 1998

[54] BIOMEDICAL ELECTRODE PROVIDING EARLY DETECTION OF ACCIDENTAL DETACHMENT

[75] Inventor: Samuel G. Netherly, Afton, Minn.

[73] Assignee: Minnesota Mining and Manufacturing Company, St. Paul, Minn.

[21] Appl. No.: 644,799

[22] Filed: May 10, 1996

[51] Int. Cl.⁶ .................................................. A61B 17/39
[52] U.S. Cl. ...................... 606/32; 606/35; 607/142; 607/152
[58] Field of Search ............ 606/32, 35; 607/142, 607/149, 152, 157

[56] References Cited

U.S. PATENT DOCUMENTS

| | | | |
|---|---|---|---|
| 4,352,359 | 10/1982 | Larimore et al. | 128/640 |
| 4,365,634 | 12/1982 | Bare et al. | 128/640 |
| 4,524,087 | 6/1985 | Engel | 427/2 |
| 4,539,996 | 9/1985 | Engel | 128/640 |
| 4,554,924 | 11/1985 | Engel | 128/640 |
| 4,715,382 | 12/1987 | Strand | 128/640 |
| 4,745,918 | 5/1988 | Feucht | 606/35 |
| 4,776,350 | 10/1988 | Grossman et al. | 128/799 |
| 4,848,348 | 7/1989 | Craighead | 128/639 |
| 4,848,353 | 7/1989 | Engel | 128/640 |
| 4,873,973 | 10/1989 | Hagen et al. | 128/303.13 |
| 5,012,810 | 5/1991 | Strand et al. | 128/640 |
| 5,042,981 | 8/1991 | Gross | 606/32 |
| 5,080,099 | 1/1992 | Way et al. | 128/640 |
| 5,114,424 | 5/1992 | Hagen et al. | 606/32 |
| 5,133,356 | 7/1992 | Bryan et al. | 128/640 |
| 5,215,087 | 6/1993 | Anderson et al. | 128/640 |
| 5,225,473 | 7/1993 | Duan | 524/388 |
| 5,276,079 | 1/1994 | Duan et al. | 524/386 |
| 5,338,490 | 8/1994 | Dietz et al. | 252/500 |
| 5,352,315 | 10/1994 | Carrier et al. | 156/267 |
| 5,362,420 | 11/1994 | Itoh et al. | 252/500 |
| 5,385,679 | 1/1995 | Uy et al. | 252/500 |
| 5,465,715 | 11/1995 | Lyons | 128/640 |
| 5,496,363 | 3/1996 | Burgio et al. | 607/152 |

FOREIGN PATENT DOCUMENTS

| | | | |
|---|---|---|---|
| 0 051 935 A2 | 5/1982 | European Pat. Off. | A61F 13/02 |
| WO 94/12585 | 6/1994 | WIPO | C09J 171/00 |
| WO 94/26950 | 11/1994 | WIPO | C23C 14/20 |
| WO 95/20634 | 8/1995 | WIPO | C09J 7/02 |

OTHER PUBLICATIONS

Kim et al., "Uniformity of Current Density Under Stimulating Electrodes" *Critical Reviews in Biomedical Engineering* vol. 17, Issue 6, pp. 585–619 (1990).

*Primary Examiner*—Lee S. Cohen
*Attorney, Agent, or Firm*—Gary L. Griswold; Walter N. Kirn; John H. Hornickel

[57] ABSTRACT

A biomedical electrode is disclosed, having a geometry of conductive plates along a longitudinal axis of the electrode such that interior edge(s) of the plate(s) adjoining the axis are curvilinear or otherwise non-parallel to the axis. The geometry permits the electrode to register an earlier detection of a CQM alarm condition if a portion of the electrode unpeels from contact with the body of a mammalian patient before the extent of unpeeling would otherwise cause a CQM alarm condition established by and issued from an electrosurgical generator.

8 Claims, 3 Drawing Sheets

BIOMEDICAL ELECTRODE PROVIDING EARLY DETECTION OF ACCIDENTAL DETACHMENT

TECHNICAL FIELD

The present invention relates generally to biomedical electrodes of the type that delivers to or receives currents from a body, such as dispersive electrodes used to return current from a patient's body in electrosurgery or cardiac stimulating electrodes used to deliver current to a patient's body.

BACKGROUND

Biomedical electrodes are used in a variety of applications and are configured to operate according to the size, type, and direction of current flowing into or out of a body of a patient.

Dispersive electrodes are used in electrosurgery. In modern surgical practice there are many times when electrosurgery is more preferable than the use of the traditional scalpel. In electrosurgery, cutting is performed by an intense electrical current passing through a cutting electrode. The surgeon directs this current to exactly where cutting is required by wielding the cutting electrode, which because of its cylindrical shape and the way it is held in the hand is commonly called an "electrosurgical pencil". By activating controls which change the characteristics of the electrical current being sent to the pencil by an electrosurgical generator, the surgeon can use the pencil either to cut or to coagulate areas of bleeding. This makes electrosurgery particularly convenient when surgery requiring extra control of blood loss is being performed. Because of concerns to minimize the transmissions of blood-borne illnesses between health care patients and health care providers, in both directions, electrosurgery is becoming increasingly important.

In electrosurgery, as in all situations where electrical current is flowing, a complete circuit must be provided to and from the current source. In this case, the current that enters the body at the pencil must leave it in another place and return to the generator. It will readily be appreciated that when current enough to deliberately cut is brought to the body of a patient in one place, great care must be taken that unintentional damage is not also done to the patient at the location where that current is leaving the body. The task of collecting the return current safely is performed by a dispersive electrode.

A dispersive electrode performs this task by providing a large surface area through which the current can pass; the same current which was at cutting intensity when focused at the small surface area at the tip of the pencil is relatively harmless, with the goal of being painless to the patient, when spread out over the large surface area of the dispersive electrode.

It will therefore be appreciated that it is critical that the intended large surface area of the dispersive electrode actually stay in intimate contact with the body of the patient. If for example, accidental tension on the cable which connects the dispersive electrode to the electrosurgical generator causes the electrode to begin to lift from the body of the patient, the current density through the portion of the dispersive electrode still in contact with the patient will rise. If it were permitted to rise sufficiently, the patient would be burned by the current flow.

To guard against this hazard, many of the most popular generator systems incorporate some sort of contact quality monitoring ("CQM") circuitry. Such circuits which can detect when the dispersive electrode does not have good attachment to the body. Generally, such CQM circuits require the use of dispersive electrodes having two or more conductive plates each separated from the other by a non-conductive or semi-conductive gap. The CQM circuitry then monitors the electrical impedance between the separated plates; only if it dispersive electrode is in contact with the body of the patient will the impedance be within a preselected range. If some mischance in the surgical suite has caused the electrode to be applied without adequate initial contact with the body or some event during surgery has caused the adequate initial contact to become inadequate, the impedance will rise outside of the preselected range and the CQM circuits will detect that rise and refuse to let any cutting current be applied or continued.

A limitation that is inherent in this system is that the impedance to be measured by the CQM circuits is dependent on the properties of the skin of the patient, which varies from one individual and the next. In order to be suitable for a wide range of persons, the preselected range of impedance values which are deemed acceptable by the CQM circuits must be rather wide. In some circumstances, this allows incipient detachment of a dispersive electrode to proceed to quite a degree before being detected, to the detriment of patient safety. The art requires a dispersive electrode which allows the detection of accidental detachment at an earlier stage than is presently possible.

SUMMARY OF THE INVENTION

The present invention solves the problems discussed above by providing a biomedical electrode where the plate-to-plate impedance which signals a problem to the CQM circuits in the electrosurgical generator increases more swiftly in the face of incipient detachment, i.e., faster than the corresponding increase in the current density which poses a danger to the patient.

The biomedical electrode of the present invention has two or more conductive plates where the edges of one or more of the plates adjoining an axis separating the conductive plates are non-parallel or otherwise curvilinearly contoured, so that the nonconductive gap along that axis between the plates is relatively narrower near at least one outside edge of the biomedical electrode orthogonal to that axis than the nonconductive gap the middle of the biomedical electrode along that axis. For purposes of this invention, the axis will be identified as a "longitudinal axis." The geometry of the arrangements of the conductive plates compared with the nonconductive gap between the plates along the longitudinal axis has a specific purpose material to the safety functions of the electrode. When the biomedical electrode is well and properly adhered to the skin of the patient, the small current that the CQM circuits introduce into the body via one conductive plate and receive from the body via the other conductive plate, in order to test the plate-to-plate impedance will preferentially pass through the patient's body adjacent the narrowest gap between the conductive plates and the impedance will be within the preselected range.

But if the biomedical electrode should accidentally begin to peel away from the body, a relatively small amount of peel-away will lift the narrower-gap portion along the longitudinal axis of the electrode off testing current from the CQM circuits to pass through the increasingly wider gap along the longitudinal axis. This increase in the size of that gap will cause the CQM circuit to then shut down the electrosurgical current at the electrosurgical pencil even though the largest part of the surface area of the conductive plates of the electrode is still in contact with the patient's body and the current density of the cutting current is still within safe limits.

The practical result of the biomedical electrode of the present invention is the creation of an "earlier" CQM alarm condition for early detection of accidental detachment of the electrode from a patient's body.

The invention provides a biomedical electrode having an electrically non-conductive backing, at least two conductive plates separated from each other along a longitudinal axis of the backing, each conductive plate contacting the electrically non-conductive backing and having an interior edge adjoining the longitudinal axis; and optionally, a field of conductive adhesive in contact with each conductive plate.

In this biomedical electrode the minimum distance separating the conductive plates along the longitudinal axis at a first point distal from the outside edge of the biomedical electrode intersecting the longitudinal axis is substantially greater than the minimum distance separating the conductive plates at a second point more proximal to that outside edge of the biomedical electrode.

In preferred embodiments, the biomedical electrode according to the invention has a body contact portion, and the ratio between the minimum distance separating the conductive plates along the longitudinal axis at a point away from the outside edge of the body contact portion and the minimum distance separating the conductive plates at a point near the outside edge of the body contact portion is greater than about 2:1.

Because it is necessary to balance the early alarm response provided by the present invention with an adequate surface area for the electrosurgical current to be received by the electrode, it is more preferable that the ratio between the minimum distance separating the conductive plates at a point away from the outside edge of the body contact portion and the minimum distance separating the conductive plates at a point near the outside edge of the body contact portion is between about 3:1 and 15:1. Most preferably, this range is between about 4:1 and 10:1.

In some preferred embodiments, there is an optional field of lossy dielectric material between the conductor plate and a surface of the electrode that can contact a body of a patient. Such an optional layer helps to reduce the amount of maximum temperature rise caused by the electrosurgical current.

Embodiments of the invention are described using the following drawings.

BRIEF DESCRIPTION OF THE DRAWING

The reference numerals refer to like parts in the several views, wherein.

EMBODIMENTS OF THE INVENTION

Figure 1:
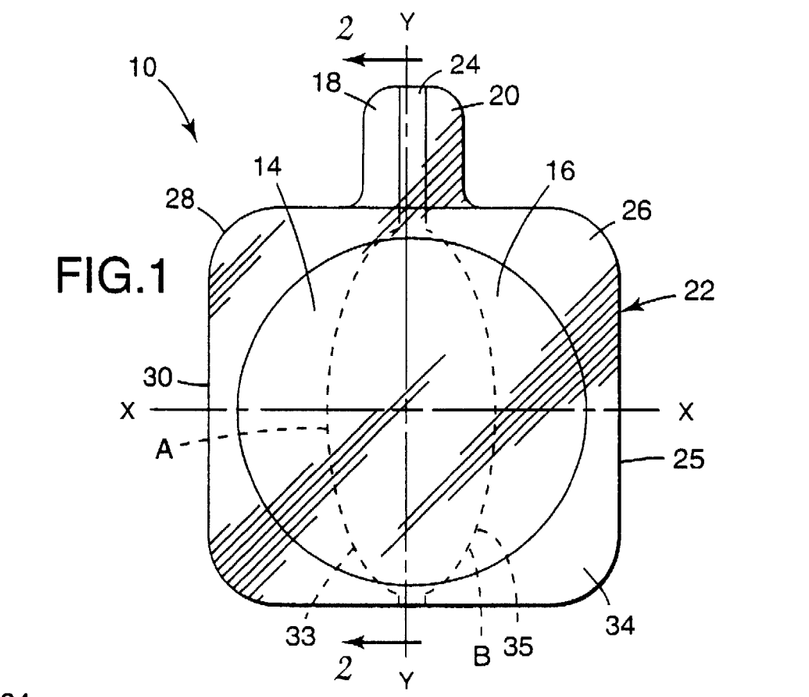
FIG. 1 is bottom perspective view according to one presently preferred embodiment of the dispersive electrode of the present invention.

FIG. 1 shows a bottom perspective view of the dispersive electrode 10. The upper surface of the electrode 10, which is on the far side in this bottom view, can be a flexible and conformable electrically non-conductive backing 12. Two conductor plates 14 and 16 are present along a longitudinal axis Y—Y matching section line 2—2, adjacent to, and can be adhered to, the electrically nonconductive backing 12. Two separate conductor plates are required for CQM circuitry because the impedance between the conductor plates 14 and 16 is measured by the above mentioned CQM circuits.

Only dispersive electrodes having two conductor plates and existing in adequate contact with the body of a patient will provide the impedance expected by the CQM circuits.

Each of the two conductor plates 14 and 16 has an extended tab 18 and 20, respectively, extending away from the body contact portion 22 of the electrode 10 for attachment of a cable assembly which connects the electrode 10 to an electrosurgical generator (not shown). In order to provide more support for the conductor plates 14 and 16, and especially for their respective tabs 18 and 20, a nonconductive support layer 24 can be laminated to the conductor plates.

The region adjacent the exterior edge 25 of the body contact portion 22 of the electrode 10 can optionally be covered with a layer 26 of a lossy dielectric material. In the embodiment of FIG. 1, the width of the layer 26 of a lossy dielectric material is widest at the corners 28, and narrowest along the edge 30 midway between the corners. As presently understood, this arrangement of the layer 26 serves best to reduce edge effect at the corners 28 of the dispersive electrode. Further explanation of the use of a lossy dielectric material can be found in copending, coassigned U.S. patent application Ser. No. 08/628,182 (Netherly et al.), the disclosure of which is incorporated by reference herein.

Preferably, the entire body contact portion 22 of electrode 10 is covered with a field 32 of conductive adhesive. Many compositions suitable for use for the field 32 of conductive adhesive are transparent, or at least translucent, and have been depicted that way in FIG. 1 for convenience in providing an explanatory drawing. The field 32 of conductive adhesive serves the dual purposes of adhering the electrode 10 to the body of the patient and of transferring the electrosurgical current between the body of the patient and the electrode for electrosurgical currents and between the electrode and the body for CQM monitoring.

Each of conductor plates 14 and 16 has an interior edge, 33 and 35 respectively, along the longitudinal axis Y—Y as seen in FIG. 1. Each of edges 33 and 35, or one of them,is curvilinear or otherwise non-parallel to the opposing edge in a manner which creates a concave-inward indent relative to the longitudinal axis Y—Y. Preferably, both edges 33 and 35 have curvilinear geometries relative to the longitudinal axis, resulting in a double concave-inward indent symmetrical about the longitudinal axis. More preferably, the double concave-inward indent is also symmetrical about an axis orthogonal to the longitudinal axis, where the second axis is a latitudinal axis X—X substantially equidistant from edges of the body contact portion 22 orthogonal to the longitudinal axis. Most preferably, as seen in FIG. 1, at the point where longitudinal axis Y—Y and latitudinal axis X—X cross orthogonally, the non-conductive gap between edges 33 and 35 is maximal.

It will be seen that at point A which is away from the outside edge 25 of the body contact portion 22 of biomedical electrode 10, the minimum distance separating the conductive plates 14 and 16 is substantially greater than the minimum distance separating the conductive plates at a point B nearer the outside edge of the body contact portion.

Figure 2:
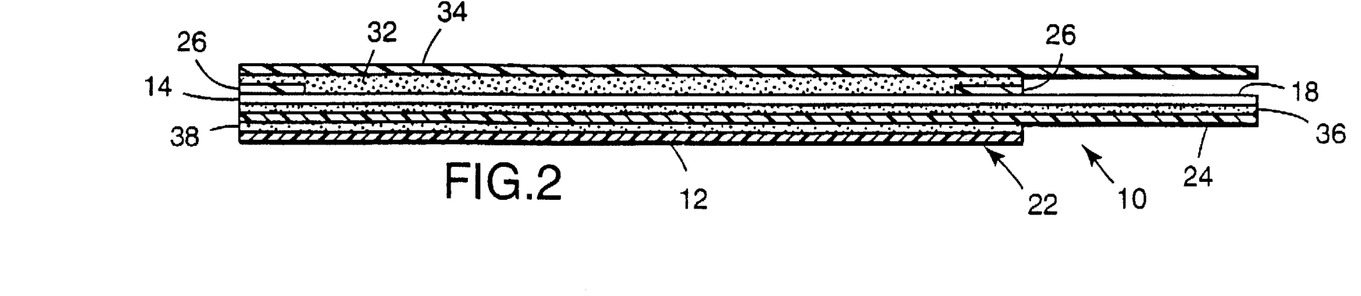
FIG. 2 is a cross-section view which is taken along section lines 2—2 in FIG. 1.

FIG. 2 shows a cross-section view of the electrode shown in FIG. 1, taken along section lines 2—2. In this view, a release liner 34 is shown adhered to the field 32 of conductive adhesive This release liner 34 protects the conductive adhesive during shipping and handling and is removed just prior to use. In this view a layer of adhesive 36 is seen adhering the support layer 24 to conductor plate 14 and its extended tab 18. Another layer of adhesive 38 is provided for adhering the electrically non-conductive backing 12 to the other side of the support layer 24.

Electrically Non-Conductive Backing

Electrically non-conductive backing 12 can be electrically insulative, and preferably is very conformable to the various contours of the mammalian body. Many materials can be used for this purpose, as will be apparent to those skilled in the art. In one presently preferred embodiment, a closed-cell foam is considered particularly suitable. One such material is commercially available as Volara brand foam from Voltek, Inc. of Massachusetts. The electrically non-conductive backing can have a thickness ranging from about 0.75 mm (0.03 inch) to about 1.5 mm (0.06 inch), and preferably 1.0 mm (0.04 inch).

Conductor Plates and Support Layer

The conductor plates 14 and 16 are conveniently made from metal, preferably in the form of a foil; a metal-containing or graphite-containing coated ink or paint, or a vapor coated metal, and most preferably, aluminum foil. If a support layer 24 is not being used, a thickness of about 0.08 mm (0.0003 inch) is considered preferred. If a support layer 24 is being used, the metal foil or vapor coated metal can be thinner because of the support provided by the support layer. A suitable support layer 24 can be made from polyethylene terephthalate (PET) film, conveniently approximately 0.05 mm (0.002 inch) thick. This allows the aluminum layer to range in thickness between about 0.0075 mm (0.0003 inch) to about 0.025 mm (0.001 inch) and preferably 0.012 mm (0.0005 inch) or allows vapor coated metal to have a minimum thickness of about 1000 Angstroms. An example of vapor coated metal on a substrate is found in PCT Publication No. WO 94/26950, the disclosure of which is incorporated by reference herein.

Conductive Adhesive

Nonlimiting examples of conductive adhesives useful in connection with the present invention include those compositions disclosed in U.S. Pat. Nos. 4,524,087 (Engel); 4,539,996 (Engel); 4,848,353 (Engel) and 5,133,356 (Bryan et al).; 5,225,473 (Duan); 5,276,079 (Duan et al); 5,338,490 (Dietz et al); 5,362,420 (Itoh et al); 5,385,679 (Uy et al); copending and coassigned applications PCT Publication Nos. WO 95/20634 and WO 94/12585; and PCT patent application Ser. Nos. US95/17079 (Docket No. 51537PCT6A); US95/16993 (Docket No. 51290PCT8A); and US95/16996 (Docket No. 48381PCT1A), the disclosures of which are incorporated by reference herein.

Release Liner

Release liner 34 can be any construction suitable for protecting the conductive adhesive 32 during shipping and handling while still releasing easily from the conductive adhesive at the time of use. One suitable liner is a 0.05 mm (0.002 inch) thick sheet of biaxially oriented polypropylene liner, commercially available as Daubert 164Z from Daubert Co. of Dixon, Ill.

Adhesive Layers

In some presently preferred embodiments, adhesive layers 36 and 38 may be used for holding other components of the electrode 10 together. Nonlimiting examples suitable adhesives 36 and 38 include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 051 935, all incorporated herein by reference.

Optionally, such adhesives can also be used to provide a border of pressure sensitive adhesive on the exterior edge 25 of electrode 10, as is disclosed in U.S. Pat. Nos. 4,524,087 (Engel); 4,539,996 (Engel); 4,848,353 (Engel).

Lossy Dielectric Layer

The layer 26 of lossy dielectric material has the performance parameters identified above in association with the ultimate performance of electrode 10 to minimize the maximum rise in temperature of tissue of a patient during electrosurgical procedures.

The lossy dielectric layer 26 can occupy an area of the body contact portion 22 ranging from about 5% to about 70% and preferably from about 40% to about 60%.

The lossy dielectric layer 26 can be made from a material and be applied in a non-uniform thickness to result in an electrical impedance gradient from the center of the body contact portion 22 to the exterior edge 25 ranging from about 30% to about 90% of the maximum impedance at exterior edge 25, and preferably from about 50% to about 70% of the maximum impedance at exterior edge of body contact portion 22.

The layer 26 can have a maximum impedance/area at the exterior edge 25 of the body contact portion 22 of the electrode 10 ranging from about 0.387 $\Omega/129$ cm$^2$ to about 20 $\Omega/129$ cm$^2$ and preferably ranging from about 1 $\Omega/129$ cm$^2$ to about 8 $\Omega/129$ cm$^2$, as determined by use of a Schlumberger 1260 spectrum impedance analyzer, operating at a frequency of 500 kHz and a constant voltage of 60 mV (RMS), and subjected to a nulling file to subtract out the effects of leadwires, connecting clips, and test fixture. A dispersive electrode of approximately 129 cm$^2$ (20 in$^2$) is the approximate size of most commercially available dispersive electrodes.

The layer 26 can have a resistance component per unit area (R/area) of the complex impedance Z of from about 0.4 $\Omega/129$ cm$^2$ to about 5 $\Omega/129$ cm$^2$ at exterior edge 25 on the dispersive electrode 10. Preferably, the layer 26 can have a resistance component per unit area ranging from about 0.5 $\Omega/129$ cm$^2$ to about 1.4 $\Omega/129$ cm$^2$. These values were determined as done for the maximum impedance per unit area.

The layer 26 can have a reactance component per unit area (X/area) of the complex impedance of from about −0.5 $\Omega/129$ cm$^2$ to about −16 $\Omega/129$ cm$^2$ at exterior edge 25 on the dispersive electrode 10. Preferably, the layer 26 can have a reactance component per unit area ranging from about −2 $\Omega/129$ cm$^2$ to about −10 $\Omega/129$ cm$^2$, using the same testing method as above for resistance per unit area and impedance per unit area.

The layer 26 can have a tan δ ranging from about 0.14 to about 1.7 at exterior edge 25 on the electrode 10, when measured at 500 kHz and a signal amplitude of 60 mV (RMS). Desirably, the tan δ can range from about 0.2 to about 1.0 at exterior edge 25 on the electrode 10, when measured at 500 Hz and a signal amplitude of 60 mV (RMS). Preferably, the tan δ ranging from about 0.2 to about 0.7 at exterior edge 25 on the electrode 10, when measured at 500 Hz and a signal amplitude of 60 mV (RMS).

Layer 26 can be made from any lossy dielectric material that can be applied to body contact portion 22 and provide the performance parameters identified above for layer 26.

Layer 26 can be formed from an ink or paint on body contact portion 22 according to electrode manufacturing techniques known to those skilled in the art. It has been found particularly convenient to provide this material in the form of a paint, which can then be screen printed or sprayed in an appropriately shaped pattern onto the electrode 10 at the proper time during its fabrication. Oil-based enamels, commercially available as Cat. nos. 7776, 7790, 7730, 7727, and 7715 from Rustoleum Corp. of Vernon Hills, Ill. are considered particularly suitable. Inks such as Summit UVII 300, UVII 800, and UVII 801 white inks, from Summit, Inc. of North Kansas City, Mo. can also be used. Additional information on the use of a lossy dielectric layer to reduce the heating caused by edge effect can be found in co-pending and co-assigned U.S. patent application Ser. No. 08/628, 182, the entire disclosure of which is hereby incorporated by reference.

Method of Making Electrodes

Electrode 10 can be made using conventional tab/pad style electrodes as described in U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); and 5,296,079 (Duan et al.), the disclosures of which are incorporated by reference herein. Generally, multiple layered electrode 10 can be assembled from rolls of starting materials for insulative electrically non-conductive backing 12, upon which is applied conductor plates 14 and 16, upon which is coated paints or inks to form lossy dielectric layer 26, upon which is coated or cured field 32 of ionically conductive pressure sensitive adhesive. Alternatively, a sheet of lossy dielectric material of a desired geometrical shape can be laminated onto conductor plates 14 and 16.

Automated machinery can be employed to make electrode 10. One skilled in the art of making electrodes can select from a variety of machinery manufacturers and manufacturing techniques to minimize manufacturing expense and waste. Some types of machinery are disclosed in U.S. Pat. Nos. 4,715,382 (Strand); 5,133,356 (Bryan et al.); and copending, coassigned U.S. patent application Ser. No. 08/343,253 (Yasis et al.), the disclosures of which are incorporated by reference herein, and U.S. Pat. No. 5,352,315 (Carrier et al.).

Embodiments of the invention are further described in the following examples.

EXAMPLE 1 (CONTROL EXAMPLE)

A dispersive biomedical electrode commercially available as 3M brand Electrosurgical Patient Plate Catalog #7180 from 3M Company of St. Paul, Minn. was shortened by cutting the biomedical electrode orthogonal to the longitudinal axis of symmetry of the biomedical electrode, leaving 4.5 inches (11.4 cm) of the skin contacting portion of the conductor plate remaining. This dispersive biomedical electrode has two conductive plates that have interior edges that are essentially parallel to the longitudinal axis and to each other at a distance of 0.25 inch (0.64 cm) apart through most of their length, although at the part of the body contact portion adjacent the extended tab the distance between the conductive plates narrows somewhat. There the minimum separation of the plates within the body contact portion narrows to 0.14 inch (0.36 cm), so it can be calculated that the ratio of the point of least separation between the interior edges of the two conductive plates and the point of greatest minimum separation between the interior edges of the two conductive plates within the body contact portion was 1.8:1. (The conductive plates are closer within the tab portion, but since they are separated one from the other by insulative material in use, their separation there has no impact on the plate-to-plate impedance.)

EXAMPLE 2

A dispersive biomedical electrode was made according to Example 1, except as illustrated in FIG. 1, a portion of each conductive plate and the conductive adhesive that covers it was excised so as to leave a concave-inwards indent or cut-out on each of the interior edges relative to the longitudinal axis.

These indents were made as smooth circular arcs with radius 8.10 inches (20.6 cm), which caused there to be a point along each interior edge where the separation from the nearest portion of the other conductive plate was at least 0.850 inches (2.2 cm). It was calculated that the ratio of the point of least separation between the interior edges of the two conductive plates and the point of greatest minimum separation between the interior edges of the two conductive plates within the body contact portion was 6.1:1.

EXAMPLE 3

A dispersive biomedical electrode was made according to Example 2, except that the indents were made as smooth circular arcs with radius 4.12 inches (10.5 cm), which caused there to be a point along each interior edge where the separation from the nearest portion of the other conductive plate was at least 1.44 inches (3.7 cm). It was calculated that the ratio of the point of least separation between the interior edges of the two conductive plates and the point of greatest minimum separation between the interior edges of the two conductive plates within the body contact portion was 10.3:1.

EXAMPLE 4

A dispersive biomedical electrode was made according to Example 2, except that the indents were made as smooth circular arcs with radius 3.08 inches (7.8 cm), which caused there to be a point along each interior edge where the separation from the nearest portion of the other conductive plate was at least 2.04 inches (5.2 cm). It was calculated that the ratio of the point of least separation between the interior edges of the two conductive plates and the point of greatest minimum separation between the interior edges of the two conductive plates within the body contact portion was 14.6:1.

Experiment 1

In turn, each of the dispersive biomedical electrodes from Examples 1–4 was placed on the anterior thigh of a human test subject, and the two conductors of biomedical electrode in the examples were connected to a Schlumberger 1260 Spectrum Impedance Analyzer. Using a constant voltage of 60 mV, the alternating current impedance between the two conductive plates of each biomedical electrode was measured over a wide range of frequencies. After these measurements were made, 2 cm of the length of each example biomedical electrode was cut off from the end of the plate opposite the connecting tab, to simulate exactly 2 cm of the biomedical electrode being peeled off the anterior thigh of the human test subject. Another set of impedance measurements was then made over the same frequency range for each plate, and this procedure was repeated for a total shortening of each plate by 4, 6, 8 and 10 cm.

The impedances for the frequencies of 125 kHz and 40 kHz were then selected for graphical presentation herein from the collected data, as being representative of the range of CQM frequencies present in the leading models of electrosurgical generators manufactured today (e.g. generators commercially available from Valleylab of Boulder, Colo. use a CQM frequency of 140 kHz, generators commercially available from Birtcher of Irvine, Calif. use a CQM frequency of 125 kHz, and generators commercially available from Aspen/Conmed of Englewood, Colo. use a CQM frequency of 39 kHz.) These graphical presentations are contained in FIGS. 3 and 4, respectively, and they plot the conductive plate-to-conductive plate alternating current impedance through the body versus the amount of the plate removed.

Figure 3:
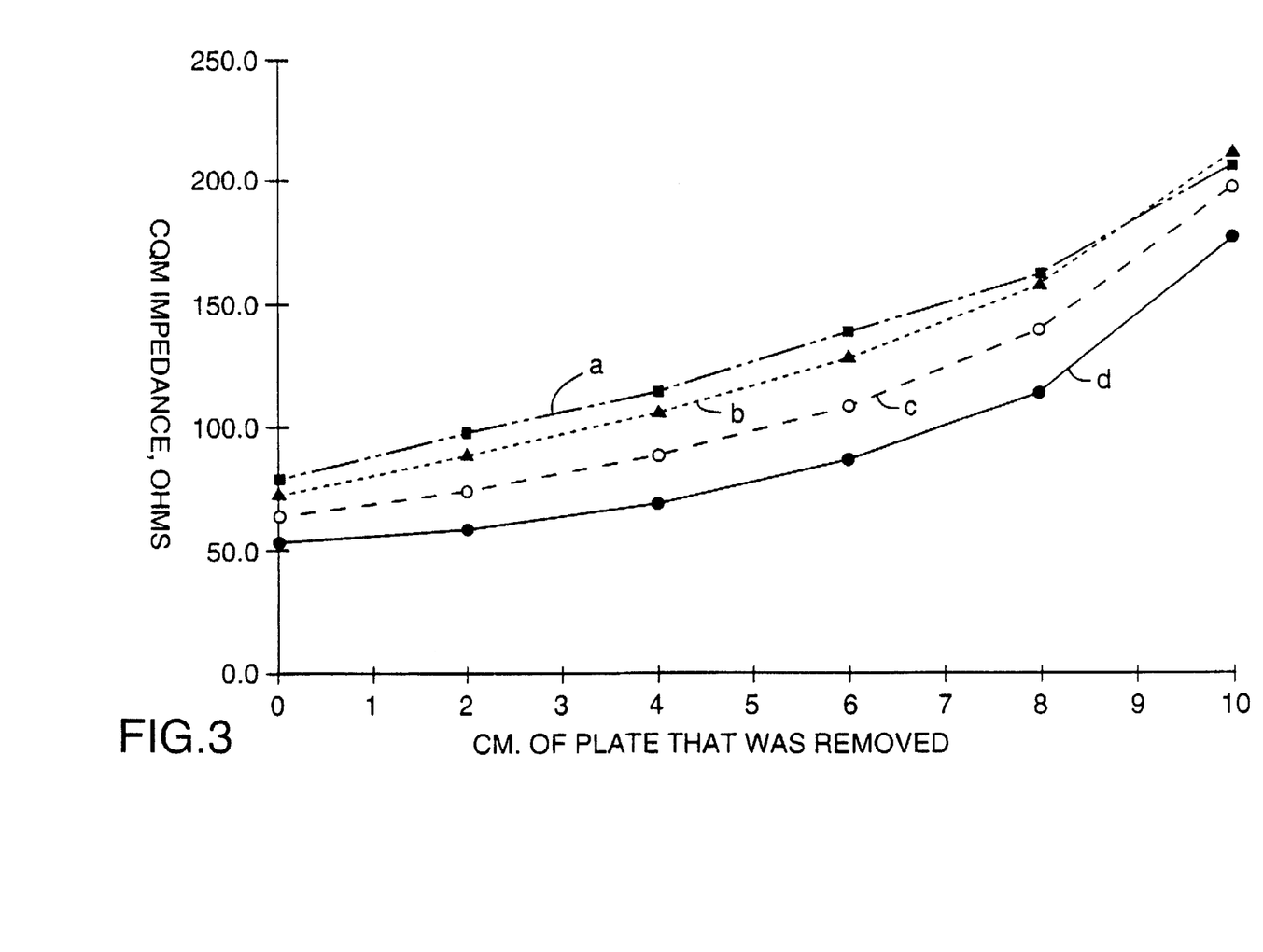
FIG. 3 is a graph of impedance in Ohms versus cm of the plate removed from the patient's body during trial experiments using a test signal of 125 kHz.
Figure 4:
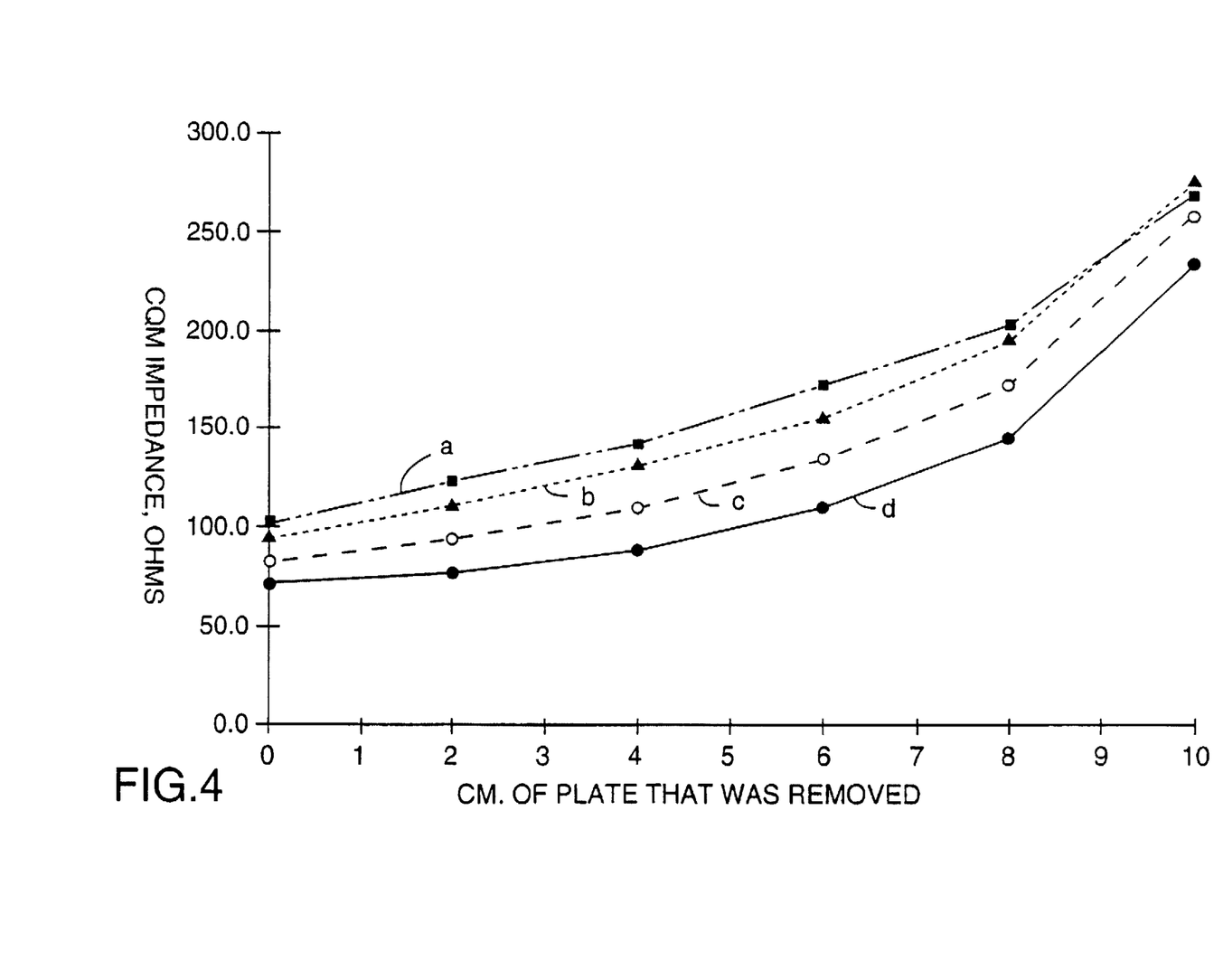
FIG. 4 is a graph of impedance in Ohms versus cm of the plate removed from the patient's body during trial experiments using a test signal of 40 kHz.

Information simulative of use conditions of the Example biomedical electrodes with each of the above named manufacturers' equipment has been extracted or calculated from the graphs and is presented in Tables #1, #2, and #3 below. Referring now to FIG. 3 and 4, it will be noted that at less than 4 cm of plate removal the slopes of the lines computing the function of alternating current impedance to amount of conductive plate removal are essentially straight. For convenient analysis, a linear curve fit of the data was done, and the results are tabulated in Tables 1–3 in the columns labeled "slope" and "intercept".

In physical terms, the intercept is the CQM impedance with the full original length of the plate attached to the human test subject, and the slope is the rate in ohms/centimeter that the CQM impedance would initially be increasing if the dispersive biomedical electrodes were being peeled back.

For all three of the manufacturers of electrosurgical generators listed above, the CQM alarm will be triggered if the impedance rises by a certain percent above its initial value. For Valleylab, a 40% rise in impedance will trigger a CQM alarm, while for Aspen/Conmed the value is 30% and for Birtcher the value is 20%. In the Tables the amount of plate removal which it was found to trigger one of these thresholds was calculated based on the initial impedance of each plate, and is shown in the column labeled "CQM Alarm Point". The next column, labeled "Ohm Increase to Alarm Point", is the ohm increase that is required to trigger the CQM alarm for that generator, and is simply the difference between the initial impedance ("Intercept") and the "CQM Alarm Point".

The "Ohm Increase to Alarm Point" is divided by the "Slope" to yield the length in centimeters that each biomedical electrode would have to be peeled back to trigger the CQM alarm with the brand of generator being simulated. As can be seen, Examples #2–#4 require substantially less of their length to be peeled back than the control Example #1 to trigger a CQM alarm. The calculated percent reduction in peel distance required to trigger a CQM alarm in each case relative to the control Example #1 is shown in the rightmost column of each table.

TABLE 1

SIMULATIVE OF A VALLEYLAB ™ GENERATOR - THE TEST VOLTAGE APPLIED AT 125 KHz, (the threshold rise in plate-to-plate impedance from initial is 40%)

| Example | Slope | Intercept | CQM Alarm Point (Ohms) | Ohm increase to alarm point | cm. of peel to CQM alarm point | % less peel over Example #1 |
|---|---|---|---|---|---|---|
| #1 | 3.81 | 53.07 | 74.29 | 21.23 | 5.57 | N.A. |
| #2 | 5.86 | 64.37 | 90.12 | 25.75 | 4.39 | 21.08 |
| #3 | 7.73 | 74.86 | 104.80 | 29.94 | 3.87 | 30.44 |
| #4 | 8.42 | 80.51 | 112.71 | 32.20 | 3.83 | 31.26 |

TABLE 2

SIMULATIVE OF AN ASPEN ™ GENERATOR - THE TEST VOLTAGE APPLIED AT 40 KHz, (the threshold rise in plate-to-plate impedance from initial is 30%)

| Example | Slope | Intercept | CQM Alarm Point (Ohms) | Ohm increase to alarm point | cm. of peel to CQM alarm point | % less peel over Example #1 |
|---|---|---|---|---|---|---|
| #1 | 4.81 | 70.10 | 91.12 | 21.03 | 4.37 | N.A. |
| #2 | 7.37 | 81.26 | 105.63 | 24.38 | 3.31 | 24.31 |
| #3 | 9.72 | 93.79 | 121.93 | 28.14 | 2.89 | 33.76 |
| #4 | 10.81 | 101.83 | 132.38 | 30.55 | 2.83 | 35.30 |

TABLE 3

SIMULATIVE OF A BIRTCHER ™ GENERATOR - THE TEST VOLTAGE APPLIED AT 125 KHz, (the threshold rise in plate-to-plate impedance from initial is 20%)

| Example | Slope | Intercept | CQM Alarm Point (Ohms) | Ohm increase to alarm point | cm. of peel to CQM alarm point | % less peel over Example #1 |
|---|---|---|---|---|---|---|
| #1 | 3.81 | 53.07 | 63.68 | 10.61 | 2.78 | N.A. |
| #2 | 5.86 | 64.37 | 77.24 | 12.87 | 2.20 | 21.08 |

TABLE 3-continued

SIMULATIVE OF A BIRTCHER ™ GENERATOR - THE TEST VOLTAGE
APPLIED AT 125 KHz, (the threshold rise in plate-to-plate impedance from initial is 20%)

| Example | Slope | Intercept | CQM Alarm Point (Ohms) | Ohm increase to alarm point | cm. of peel to CQM alarm point | % less peel over Example #1 |
|---|---|---|---|---|---|---|
| #3 | 7.73 | 74.86 | 89.83 | 14.97 | 1.94 | 30.44 |
| #4 | 8.42 | 80.51 | 96.61 | 16.10 | 1.91 | 31.26 |

Various modifications and alterations of the present invention will be apparent to those skilled in the art without departing from the scope and spirit of this invention, and it should be understood that this invention is not limited to the illustrative embodiments set forth herein. For example, it should not be construed that the profile of the indent provided on the interior edge of the conductive plates illustrative embodiments set forth herein. For example, it should not be construed that the profile of the indent provided on the interior edge of the conductive plates needs to have a continuous curve or needs to be symmetrical or needs to be present on both of the conductive plates. The claims follow.

What is claimed is:

1. A biomedical electrode, comprising:

an electrically non-conductive backing;

two conductive plates required for Contact Quality Monitoring circuitry separated from each other along a longitudinal axis of the backing, each conductive plate contacting the electrically non-conductive backing, and each conductive dilate having a curvilinear interior edge adjoining the longitudinal axis which edge is also symmetrical about an axis orthogonal to the longitudinal exit; and optionally, a field of conductive adhesive in contact with both the conductive plates, wherein the minimum distance separating the conductive plates along the longitudinal axis at a first point distal from an outside edge of the biomedical electrode intersecting the longitudinal axis is substantially greater than the minimum distance separating the conductive plates at a second point more proximal to the outside edge of the biomedical electrode.

2. The biomedical electrode according to claim 1, further comprising a field of lossy dielectric material between the conductor plates and a surface of the electrode that can contact a body of a patient.

3. The biomedical electrode according to claim 1, wherein the conductive plates have a body contacting portion and wherein the ratio between the minimum distance separating the conductive plates along the longitudinal axis at a point away from the outside edge of the body contact portion and the minimum distance separating the conductive plates at a point near the outside edge of the body contact portion is greater than about 2:1.

4. The biomedical electrode, according to claim 3, wherein the ratio between the minimum distance separating the conductive plates at a point away from the outside edge of the body contact portion and the minimum distance separating the conductive plates at a point near the outside edge of the body contact portion is between about 3:1 and 15:1.

5. The biomedical electrode, according to claim 4, wherein the ratio between the minimum distance separating the conductive plates at a point away from the outside edge of the body contact portion and the minimum distance separating the conductive plates at a point near the outside edge of the body contact portion is between about 4:1 and 10:1.

6. An electrosurgical CQM circuit, comprising:

(a) an electrosurgical generator having CQM circuit;

(b) a biomedical electrode; and (c) electrical connections between the generator and the electrode, wherein the biomedical electrode, comprises an electrically nonconductive backing;

two conductive plates required for Contact Quality Monitoring circuitry separated from each other along a longitudinal axis of the backing, each conductive plate contacting the electrically non-conductive backing and each conductive plate having a curvilinear interior edge adjoining the longitudinal axis which edgei s also symmetrical about an axis orthogonal to the longitudinal axis; and optionally, a field of conductive adhesive in contact with both the conductive plates, wherein the minimum distance separating the conductive plates along the longitudinal axis at a first point distal from an outside edge of the biomedical electrode intersecting the longitudinal axis is substantially greater than the minimum distance separating the conductive plates at a second point more proximal to the outside edge of the biomedical electrode.

7. An electrosurgical system, comprising:

(a) an electrosurgical generator having CQM circuitry;

(b) a biomedical electrode;

(c) an electrosurgical pencil electrically connected to the generator; and (d) electrical connections between the generator and the electrode, wherein the biomedical electrodes comprises an electrically non-conductive backing;

two conductive plates required for Contact Quality Monitoring circuitry separated from each other along a longitudinal axis of the backing, each conductive plate contacting the electrically non-conductive backing, and each conductive plate having a curvilinear interior edge adjoining the longitudinal axis which edge is also symmetrical about an axis orthogonal to the longitude axis; and optionally, a field of conductive adhesive in contact with both the conductive plates, wherein the minimum distance separating the conductive plates along the longitudinal axis at a first point distal from an outside edge of the biomedical electrode intersecting the longitudinal axis is substantially greater than the minimum distance separating the conductive plates at a second point more proximal to the outside edge of the biomedical electrode.

8. A method of early detection of an electrosurgical CQM alarm condition, comprising the steps of:

(a) contacting a biomedical electrode to the body of a mammalian patient;

(b) sounding an alarm when a portion of the biomedical electrode separates from contact with the body of the patient, wherein the portion of the biomedical electrode separated lies along a longitudinal axis of the biomedical electrode, wherein the biomedical electrode comprises an electrically non-conductive backing and two conductive plates;

wherein the two conductive plates require for Contact Quality Monitoring circuitry are separated from each other alone the longitudinal axis, each conductive plate contacting the electrically non-conductive backing, and each conductive plate having a curvilinear interior edge adjoining longitudinal axis which edge is also symmetrical about an axis orthogonal to the longitudinal axis and wherein a minimum distance separating the conductive plates along the longitudinal axis at a first point distal from an outside edge of the biomedical electrode intersecting the longitudinal axis is substantially greater than the minimum distance separating the conductive plates at a second point more proximal to the outside edge of the biomedical electrode.

* * * * *

UNITED STATES PATENT AND TRADEMARK OFFICE
CERTIFICATE OF CORRECTION

PATENT NO.: 5,797,902

DATED: August 25, 1998

INVENTOR(S): Samuel G. Netherly

It is certified that error appears in the above-identified patent and that said Letters Patent is hereby corrected as shown below:

Column 11, line 36, "exit" should read as  - axis –

Column 12, line 22, "circuit" should read as  - circuitry –

Column 12, line 34, "edgei s" should read as  -edge is -

Signed and Sealed this

Eighth Day of December, 1998

Attest:

Attesting Officer

BRUCE LEHMAN

Commissioner of Patents and Trademarks